(12) United States Patent
Julian

(10) Patent No.: US 7,623,916 B2
(45) Date of Patent: Nov. 24, 2009

(54) IMPLANTABLE CARDIAC STIMULUS DEVICES AND METHODS WITH INPUT RECHARGE CIRCUITRY

(75) Inventor: Marcus Julian, Encinitas, CA (US)

(73) Assignee: Cameron Health, Inc., San Clemente, CA (US)

( * ) Notice: Subject to any disclaimer, the term of this patent is extended or adjusted under 35 U.S.C. 154(b) by 336 days.

(21) Appl. No.: 11/613,850

(22) Filed: Dec. 20, 2006

(65) Prior Publication Data

US 2008/0154350 A1   Jun. 26, 2008

(51) Int. Cl.
*A61N 1/00* (2006.01)
(52) U.S. Cl. ...................................................... 607/11
(58) Field of Classification Search ............... 607/4–28; 600/508–519; 324/678
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |

(Continued)

FOREIGN PATENT DOCUMENTS

DE          29801807          7/1998

(Continued)

OTHER PUBLICATIONS

U.S. Appl. No. 11/441,516 to Sanghera et al., filed May 26, 2006.

(Continued)

*Primary Examiner*—George Manuel
*Assistant Examiner*—Robert N Wieland
(74) *Attorney, Agent, or Firm*—Pramudji Wendt & Tran, LLP; Ari Pramudji; Mark Schroeder

(57) ABSTRACT

An illustrative embodiment includes an implantable cardiac stimulus device comprising input circuitry configured to reduce the time required to return to small signal operation after a disturbance of small signal operation. In another illustrative embodiment, the present invention includes methods for operating an implantable cardiac stimulus device to reduce the time required to return to small signal operation after a disturbance of small signal operation. In yet additional embodiments, the initiation of small signal operation after a change in sensing vector and/or after delivery of a stimulus to the patient is improved by the inclusion of input circuitry and/or the use of methods adapted to reduce the time needed to reach small signal operation.

13 Claims, 12 Drawing Sheets

U.S. PATENT DOCUMENTS

| | | | |
|---|---|---|---|
| 4,407,288 A | 10/1983 | Langer et al. | |
| 4,424,818 A | 1/1984 | Doring et al. | |
| 4,450,527 A | 5/1984 | Sramek | |
| 4,548,209 A | 10/1985 | Weilders et al. | |
| 4,567,900 A | 2/1986 | Moore | |
| 4,574,813 A | 3/1986 | Regan | |
| 4,595,009 A | 6/1986 | Leinders | |
| 4,602,637 A | 7/1986 | Elmqvist et al. | |
| 4,603,705 A | 8/1986 | Speicher et al. | |
| 4,693,253 A | 9/1987 | Adams | |
| 4,727,877 A | 3/1988 | Kallok | |
| 4,750,494 A | 6/1988 | King | |
| 4,765,341 A | 8/1988 | Mower et al. | |
| 4,768,512 A | 9/1988 | Imran | |
| 4,800,883 A | 1/1989 | Winstrom | |
| 4,830,005 A | 5/1989 | Woskow | |
| 4,944,300 A | 7/1990 | Saksena | |
| 4,991,583 A * | 2/1991 | Silvian | 607/13 |
| 5,044,374 A | 9/1991 | Lindemans et al. | |
| 5,105,810 A | 4/1992 | Collins et al. | |
| 5,105,826 A | 4/1992 | Smits et al. | |
| 5,109,842 A | 5/1992 | Adinolfi | |
| 5,129,392 A | 7/1992 | Bardy et al. | |
| 5,133,353 A | 7/1992 | Hauser | |
| 5,144,946 A | 9/1992 | Weinberg et al. | |
| 5,184,616 A | 2/1993 | Weiss | |
| 5,191,901 A | 3/1993 | Dahl et al. | |
| 5,203,348 A | 4/1993 | Dahl et al. | |
| 5,215,081 A | 6/1993 | Ostroff | |
| 5,230,337 A | 7/1993 | Dahl et al. | |
| 5,255,692 A | 10/1993 | Neubauer et al. | |
| 5,261,400 A | 11/1993 | Bardy | |
| 5,300,106 A | 4/1994 | Dahl et al. | |
| 5,313,953 A | 5/1994 | Yomtov et al. | |
| 5,331,966 A | 7/1994 | Bennett et al. | |
| 5,342,407 A | 8/1994 | Dahl et al. | |
| 5,366,496 A | 11/1994 | Dahl et al. | |
| 5,376,103 A | 12/1994 | Anderson et al. | |
| 5,376,104 A | 12/1994 | Sakai et al. | |
| 5,385,574 A | 1/1995 | Hauser et al. | |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,439,485 A | 8/1995 | Mar et al. | |
| 5,441,518 A | 8/1995 | Adams | |
| 5,447,521 A | 9/1995 | Anderson et al. | |
| 5,476,503 A | 12/1995 | Yang | |
| 5,509,923 A | 4/1996 | Middleman et al. | |
| 5,509,928 A | 4/1996 | Acken | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,597,956 A | 1/1997 | Ito et al. | |
| 5,601,607 A | 2/1997 | Adams | |
| 5,603,732 A | 2/1997 | Dahl et al. | |
| 5,607,455 A | 3/1997 | Armstrong | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,319 A | 8/1997 | Kroll | |
| 5,658,321 A | 8/1997 | Fayram et al. | |
| 5,674,260 A | 10/1997 | Weinberg | |
| 5,690,648 A | 11/1997 | Fogarty et al. | |
| 5,690,683 A | 11/1997 | Haefner et al. | |
| 5,697,953 A | 12/1997 | Kroll et al. | |
| 5,713,926 A | 2/1998 | Hauser et al. | |
| 5,766,226 A | 6/1998 | Pedersen | |
| 5,776,169 A | 7/1998 | Schroeppel | |
| 5,814,090 A | 9/1998 | Latterell et al. | |
| 5,827,326 A | 10/1998 | Kroll et al. | |
| 5,836,976 A | 11/1998 | Min et al. | |
| 5,843,132 A | 12/1998 | Ilvento | |
| 5,895,414 A | 4/1999 | Sanchez-Zambrano | |
| 5,904,705 A | 5/1999 | Kroll et al. | |
| 5,919,211 A | 7/1999 | Adams | |
| 5,919,222 A | 7/1999 | Hjelle et al. | |
| 5,925,069 A | 7/1999 | Graves et al. | |
| 5,935,154 A | 8/1999 | Westlund | |
| 5,941,904 A | 8/1999 | Johnston et al. | |
| 5,957,956 A | 9/1999 | Kroll et al. | |
| 6,014,586 A | 1/2000 | Weinberg et al. | |
| 6,026,325 A | 2/2000 | Weinberg et al. | |
| 6,058,328 A | 5/2000 | Levine et al. | |
| 6,093,173 A | 7/2000 | Balceta et al. | |
| 6,095,987 A | 8/2000 | Shmulewitz et al. | |
| H1905 H | 10/2000 | Hill | |
| 6,128,531 A | 10/2000 | Campbell-Smith | |
| 6,144,866 A | 11/2000 | Miesel et al. | |
| 6,144,879 A | 11/2000 | Gray | |
| 6,148,230 A | 11/2000 | KenKnight | |
| 6,185,450 B1 | 2/2001 | Seguine et al. | |
| 6,266,567 B1 | 7/2001 | Ishikawa et al. | |
| 6,278,894 B1 | 8/2001 | Salo et al. | |
| 6,280,462 B1 | 8/2001 | Hauser et al. | |
| 6,334,071 B1 | 12/2001 | Lu | |
| 6,345,198 B1 | 2/2002 | Mouchawar et al. | |
| 6,411,844 B1 | 6/2002 | Kroll et al. | |
| 6,647,292 B1 | 11/2003 | Bardy et al. | |
| 6,721,597 B1 | 4/2004 | Bardy et al. | |
| 6,754,528 B2 | 6/2004 | Bardy et al. | |
| 6,778,860 B2 | 8/2004 | Ostroff et al. | |
| 6,788,974 B2 | 9/2004 | Bardy et al. | |
| 6,834,204 B2 | 12/2004 | Ostroff et al. | |
| 6,856,835 B2 | 2/2005 | Bardy et al. | |
| 6,865,417 B2 | 3/2005 | Rissmann et al. | |
| 6,866,044 B2 | 3/2005 | Bardy et al. | |
| 6,927,721 B2 | 8/2005 | Ostroff et al. | |
| 6,937,907 B2 | 8/2005 | Bardy et al. | |
| 6,950,705 B2 | 9/2005 | Bardy et al. | |
| 6,952,608 B2 | 10/2005 | Ostroff | |
| 6,952,610 B2 | 10/2005 | Ostroff et al. | |
| 6,954,670 B2 | 10/2005 | Ostroff | |
| 6,980,856 B2 | 12/2005 | Sullivan et al. | |
| 6,988,003 B2 | 1/2006 | Bardy et al. | |
| 6,996,434 B2 | 2/2006 | Marcovecchio et al. | |
| 7,020,523 B1 | 3/2006 | Lu et al. | |
| 7,027,858 B2 | 4/2006 | Cao et al. | |
| 7,039,459 B2 | 5/2006 | Bardy et al. | |
| 7,039,463 B2 | 5/2006 | Marcovecchio | |
| 7,039,465 B2 | 5/2006 | Bardy et al. | |
| 7,043,299 B2 | 5/2006 | Erlinger et al. | |
| 7,062,329 B2 | 6/2006 | Ostroff | |
| 7,065,407 B2 | 6/2006 | Bardy et al. | |
| 7,065,410 B2 | 6/2006 | Bardy et al. | |
| 7,069,080 B2 | 6/2006 | Bardy et al. | |
| 7,076,294 B2 | 7/2006 | Bardy et al. | |
| 7,076,296 B2 | 7/2006 | Rissmann et al. | |
| 7,090,682 B2 | 8/2006 | Sanders et al. | |
| 7,092,754 B2 | 8/2006 | Bardy et al. | |
| 7,120,495 B2 | 10/2006 | Bardy et al. | |
| 7,120,496 B2 | 10/2006 | Bardy et al. | |
| 7,146,212 B2 | 12/2006 | Bardy et al. | |
| 7,149,575 B2 | 12/2006 | Ostroff et al. | |
| 7,181,274 B2 | 2/2007 | Rissmann et al. | |
| 7,262,609 B2 * | 8/2007 | Reynolds | 324/678 |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |

| | | | |
|---|---|---|---|
| 2002/0035381 | A1 | 3/2002 | Bardy et al. |
| 2002/0095184 | A1 | 7/2002 | Bardy et al. |
| 2002/0107544 | A1 | 8/2002 | Ostroff et al. |
| 2002/0107545 | A1 | 8/2002 | Rissmann et al. |
| 2003/0088279 | A1 | 5/2003 | Rissmann et al. |
| 2003/0135125 | A1 | 7/2003 | Lu et al. |
| 2004/0254611 | A1 | 12/2004 | Palreddy et al. |
| 2004/0254613 | A1 | 12/2004 | Ostroff et al. |
| 2005/0049644 | A1 | 3/2005 | Warren et al. |
| 2006/0085038 | A1 | 4/2006 | Linder et al. |

FOREIGN PATENT DOCUMENTS

| | | |
|---|---|---|
| EP | 0095727 | 12/1983 |
| EP | 0316616 | 5/1989 |
| EP | 0347353 | 12/1989 |
| EP | 0517494 | 12/1992 |
| EP | 0518599 | 12/1992 |
| EP | 0536873 | 4/1993 |
| EP | 0586858 | 3/1994 |
| EP | 0627237 | 12/1994 |
| EP | 0641573 | 3/1995 |
| EP | 0677301 | 10/1995 |
| EP | 0917887 | 5/1999 |
| EP | 0923130 | 6/1999 |
| EP | 1000634 | 5/2000 |
| WO | 9319809 | 10/1993 |
| WO | 9729802 | 8/1997 |
| WO | 9825349 | 6/1998 |
| WO | 9903534 | 1/1999 |
| WO | 9937362 | 7/1999 |
| WO | 9953991 | 10/1999 |
| WO | 0041766 | 7/2000 |
| WO | 0050120 | 8/2000 |
| WO | 0143649 | 6/2001 |
| WO | 0156166 | 8/2001 |
| WO | 0222208 | 3/2002 |
| WO | 0224275 | 3/2002 |
| WO | 02068046 | 9/2002 |
| WO | 03018121 | 3/2003 |

OTHER PUBLICATIONS

U.S. Appl. No. 11/497,204 to Phillips, filed Aug. 1, 2006.
International Search Report for PCT/U52007/088380; published Jan. 29, 2009 as part of WO 2008-079979 A3.
Bardy, Gust H. et al., "Multicenter Experience with a Pectoral Unipolar Implantable Cardioverter-Defibrillator," JACC, Aug. 1996, vol. 28, No. 2, pp. 400-410.
Friedman, Richard A. et al., "Implantable Defibrillators In Children: From Whence to Shock," Journal of Cardiovascular Electrophysiology, vol. 12, No. 3, Mar. 2001, pp. 361-362.
Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," Journal of Cardiovascular Electrophysiology, vol. 12, No. 3, Mar. 2001, pp. 356-360.
Higgins, Steven L. et al., "The First Year Experience with the Dual Chamber ICD," PACE, Jan. 2000, vol. 23, pp. 18-25.
Mirowski, M. et al., "Automatic Detection and Defibrillation of Lethal Arrhythmias-A New Concept," JAMA, vol. 213, No. 4, Jul. 27, 1970, pp. 615-616.
Olson, Walter H. et al., "Onset and Stability for Ventricular Tachyarrhythmia Detection in an Implantable Pacer-Cardioverter-Defibrillator," IEEE, (1987) pp. 167-170.
Schuder, John C., "Completely Implanted Defibrillator," JAMA, vol. 214, No. 6, Nov. 9, 1970. p. 1123 (single sheet).
Schuder, John C. et al., "Experimental Ventricular Defibrillation with an Automatic and Completely Implanted System," Trans. Amer. Soc. Artif. Int. Organs, vol. XVI (1970) pp. 207-212.
Schuder, John C., "The Role of an Engineering Oriented Medical Research Group in Developing Improved Methods and Devices for Achieving Ventricular Defibrillation: The University of Missouri Experience," PACE, vol. 16, Jan. 1993, pp. 95-124.
Schuder, John C. et al., "Standby Implanted Defibrillators," Arch Intern. Med, vol. 127, Feb. 1971, P. 317 (single sheet).
Schuder, John C. et al., "Transthoracic Ventricular Defibrillation in the Dog with Truncated and Untruncated Exponential Stimuli," IEEE Transactions on Bio-Medical Engineering, vol. BME-18, No. 6, Nov. 1971, pp. 410-415.
Schwacke, H. et al., "Komplikationen mit Sonden bei 340 Patienten mit einem Implantierbaren Kardioverter/Defibrillator," Z Kardiol (1999)vol. 88, No. 8, pp. 559-565.
Throne, Robert D., "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.
Tietze U. et al., "Halbleiter-Schaltungstechnik," © Springer-Verlag (Berlin, Germany), (1991) pp. 784-786.
Valenzuela, Terrence D. et al. "Outcomes of Rapid Defibrillation by Security Officers After Cardiac Arrest in Casinos," The New England Journal of Medicine, Oct. 26, 2000, vol. 343, No. 17, pp. 1206-1209.
Walters, R.A. et al., "Analog to Digital Conversion Techniques in Implantable Devices," Annual International Conference of the IEEE Engineering in Medicine and Biology Society, vol. 13 No. 4 (1991) p. 1674-1676.

* cited by examiner

IMPLANTABLE CARDIAC STIMULUS DEVICES AND METHODS WITH INPUT RECHARGE CIRCUITRY

FIELD

The present invention is related to the field of implantable medical devices. More specifically, the present invention relates to implantable cardiac stimulus devices.

BACKGROUND

Implantable cardiac stimulus devices typically monitor cardiac function of a receiving patient by capturing signal from implanted electrodes. Small signal operation refers to the state in which the input circuitry of an implanted cardiac stimulus device predictably amplifies the received signal. Delivery of a stimulus, however, can disrupt small signal operation. Devices that include circuitry adapted for quick recovery to small signal operation after disturbance of small signal operation are desired.

SUMMARY

An illustrative embodiment includes an implantable cardiac stimulus device comprising input circuitry configured to reduce the time required to return to small signal operation after a disturbance of small signal operation. Another illustrative embodiment includes methods for operating an implantable cardiac stimulus device to reduce the time required to return to small signal operation after a disturbance of small signal operation. In yet additional embodiments, the initiation of small signal operation after a change in sensing vector and/or after delivery of a stimulus to the patient is improved by the inclusion of input circuitry and/or the use of methods adapted to reduce the time needed to reach small signal operation.

DETAILED DESCRIPTION

The following detailed description should be read with reference to the drawings. The drawings, which are not necessarily to scale, depict illustrative embodiments and are not intended to limit the scope of the invention.

Some of the following illustrative embodiments relate to recovery after delivery of a stimulus to a patient. The stimulus may be a cardioversion or defibrillation stimulus having a suitable waveform, duration and amplitude. The stimulus may also be a pacing stimulus with a suitable waveform, duration and amplitude. Some of the following embodiments provide illustrative durations for select time periods in a method relating to post-stimulus recovery for the device, but other embodiments may use different durations, as suits the particular application, patient, and/or device configuration.

Figure 1A:
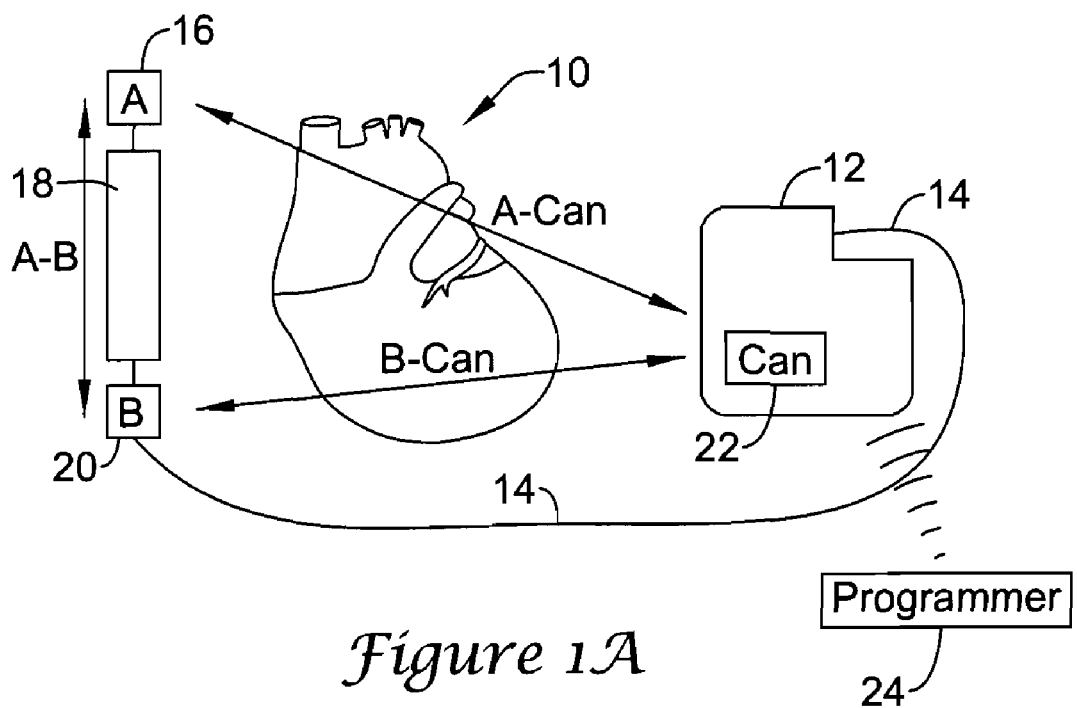
FIGS. 1A-1B, respectively, show subcutaneous and transvenous implanted cardiac stimulus systems relative to the heart.
Figure 1B:
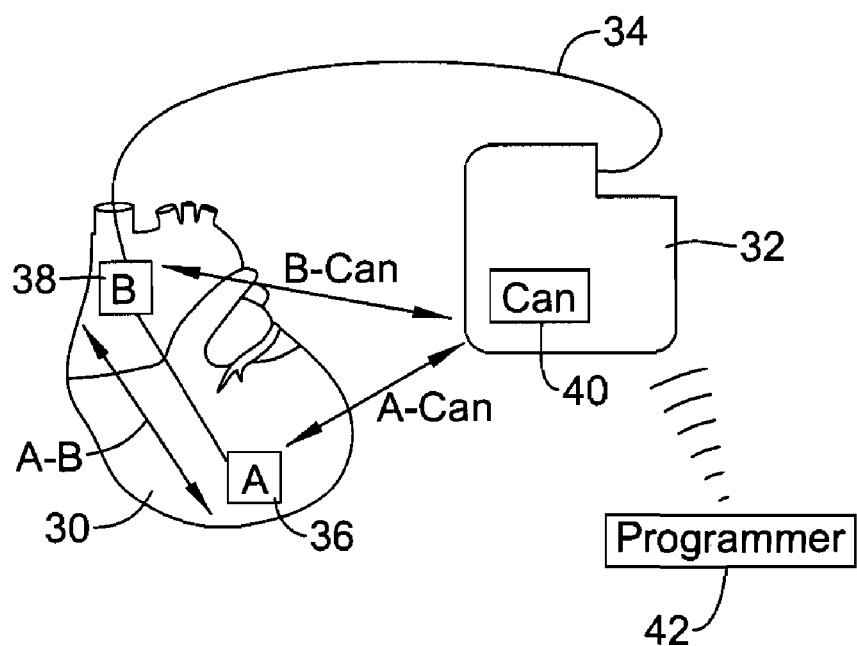

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister 12 and includes sensing electrode A 16, coil electrode 18, and sensing electrode B 20. A can electrode 22 is shown on the canister 12. Several vectors for sensing are therefore available including A-can, B-can, and A-B. It should be noted that the use of the coil electrode 18 as a sensing electrode is also possible. Illustrative subcutaneous systems are shown in U.S. Pat. Nos. 6,647,292 and 6,721,597, and the disclosures of these patents are incorporated herein by reference.

Some embodiments include a unitary system having two or more electrodes on a housing as set forth in the '292 patent, rather than that which is shown in FIG. 1A. A system having a conformal housing with one or more electrodes thereon, and optionally an additional lead, may also be used. An illustrative example of a conformal housing is shown in U.S. Pat. No. 6,788,974, the disclosure of which is also incorporated herein by reference. Different configurations of the system, including changes to the positioning of the lead 14 and can 12 relative to the heart 10 may also be used.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. Additional electrodes for sensing or stimulus delivery may also be included, and also may be used for sensing in some embodiments. In the illustrative example, electrode A 36 is located generally in the patient's ventricle, and electrode B 38 is located generally in the patient's atrium. The lead 34 may be anchored into the patient's myocardium. Again, a can electrode 40 is shown on the canister 32. With this system, plural sensing vectors may be defined as well. Other lead and electrode configurations may also be used.

In both FIGS. 1A and 1B, one or more sensing electrodes may also be used for stimulus delivery. Some embodiments of the present invention may be used in combination systems that may include sensing vectors defined between two subcutaneous electrodes, a subcutaneous electrode and a transvenous electrode, and two transvenous electrodes.

In the configurations of FIGS. 1A and 1B, there are multiple sensing vectors available. Detection of cardiac function along one of these sensing vectors allows the implanted cardiac stimulus system to determine whether treatment is indicated due to the detection and identification of a malignant condition such as, for example, a ventricular tachycardia. Illustrative methods of selecting an appropriate sensing vector are shown, for example, in U.S. patent application Ser. No. 10/901,258, filed Jul. 27, 2004, now U.S. Pat. No. 7,392,085 and titled MULTIPLE ELECTRODE VECTORS FOR IMPLANTABLE CARDIAC TREATMENT DEVICES and U.S. patent application Ser. No. 11/441,516, filed May 26, 2006, published as US 2007-0276447 A1, and titled IMPLANTABLE MEDICAL DEVICES AND PROGRAMMERS ADAPTED FOR SENSING VECTOR SELECTION, each of which is incorporated herein by reference. With multiple sensing vectors available, the implanted devices 12, 32 may include associated switching arrays that allow selection of a desired vector.

The systems shown in FIGS. 1A-1B may include operational circuitry and a power source housed within the respective canisters. The power source may be, for example, a battery or bank of batteries. The operational circuitry may be configured for and include such controllers, microcontrollers, logic devices, memory, and the like, as selected, needed, or desired for performing the illustrative methods set forth herein. The operational circuitry may further include a charging sub-circuit and a power storage sub-circuit (for example, a capacitor or bank of capacitors) for building up a stored voltage for cardiac stimulus in the form of cardioversion and/or defibrillation stimuli. The operational circuitry may also be adapted to provide a pacing output. Both cardioversion/defibrillation and pacing sub-circuitry and capabilities may be incorporated into a single device. The methods discussed herein may be embodied in any suitable manner, for example, in dedicated hardware and/or instruction sets for operating the operational circuitry and/or in the form of machine-readable media (optical, electrical, magnetic, etc.) embodying such instructions and instruction sets.

Each of the devices 12, 32 may further include such components as would be appropriate for communication (such as RF communication, inductive telemetry or other suitable communication linkage) with an external device such as a programmer. To this end, programmers 24 (FIG. 1A) and 42 (FIG. 1B) are also shown. For example, during an implantation procedure, once the implantable device 12, 32 and leads (if included) are placed, the programmer 24, 42 may be used to activate and/or direct and/or observe diagnostic or operational tests. After implantation, the programmer 24, 42 may be used to non-invasively determine the status and history of the implanted device. The programmers 24, 42 in combination with the implanted devices 12, 32 may also allow annunciation of statistics, errors, history and potential problems to the user/physician, and may also allow for updating of instruction protocols in the implanted devices 12, 32.

Figure 2:
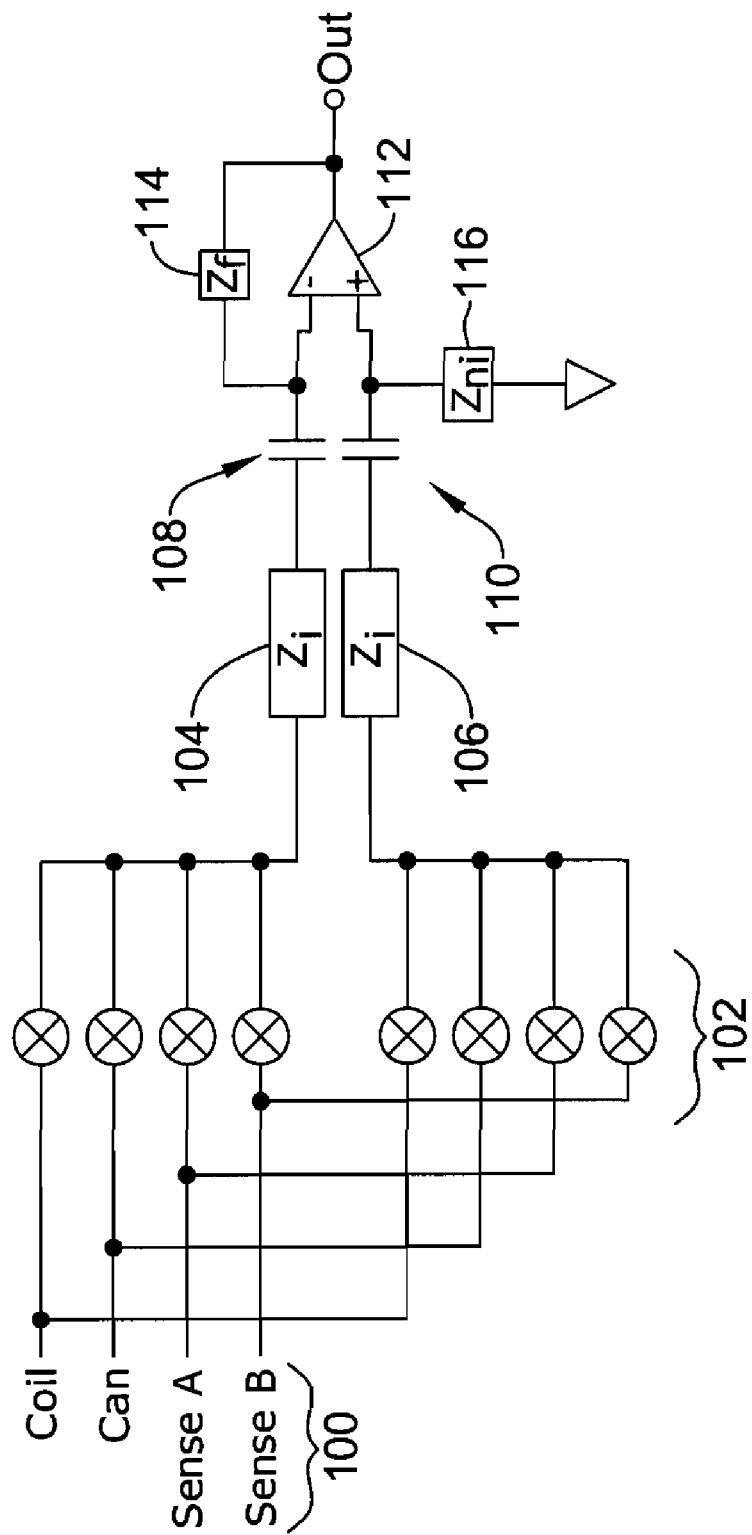
FIG. 2 is a schematic illustrating input circuitry for a device having a plurality of available sensing vectors.

FIG. 2 is a schematic illustrating input circuitry for a device having a plurality of available sensing vectors. As shown at 100, there are four available electrodes in the example system, Coil, Can, Sense A and Sense B. These may correspond to the electrodes shown in either of FIGS. 1A or 1B. A switching array is shown at 102, and is configured for selection of any pair of the four available electrodes 100 in either polarity. The switches in the switching array 102, as well as the other switches used in the following illustrative embodiments, may take any suitable form including electric, electromechanical, etc. In an illustrative embodiment, the switches are MOSFET switches, although switches based on bipolar, junction, and SCR devices may instead be used.

The incoming signals, once selected by the switching array 102, encounter input impedances as shown at 104, 106. Next, coupling capacitors 108, 110 are included to filter low frequency noise such as any DC offset between the selected sensing electrodes 100. The signal then goes to the ECG Amplifier 112, which provides amplification to a level that is appropriate for further use in the system. A filter 114 is also provided as feedback across the ECG Amplifier 112, and may be configured as a low-pass filter, removing higher frequency noise such as myopotentials from skeletal muscle and the like. An impedance, $Z_{ni}$ 116, couples the non-inverting input to ground.

In some embodiments, the switching array 102 may be reconfigured during operation to change the selected sensing vector. This may occur, for example, if the signal-to-noise ratio (SNR) of one vector drops below a suitable level, or if difficulties in cardiac event detection occur and/or persist. During steady state operation, the coupling capacitors 108, 110 will store some voltage thereon associated with the DC state of the electrodes selected for sensing. When a new sensing vector is chosen, a different "pair" of electrodes is selected, since at least one of the electrodes that is coupled via the switching array 102 changes. With at least one electrode being switched, the DC state of the system may change and require the feedback loop, operating through the filtering impedance $Z_f$, to change the voltage on coupling capacitor 108 to account for the change in the DC state of the electrodes. Meanwhile, the other coupling capacitor 110 may also undergo some DC change, with current flowing through impedance $Z_{ni}$ 116. With the configuration shown and in an implantable medical device, it can be difficult to quickly achieve small signal operation once disrupted. For example, relatively large impedances may be used to reduce power consumption, while the output limits of the ECG Amplifier 112 may be limited to reduce power consumption or simply because the entire sensing system operates at a relatively low voltage.

Figure 3:
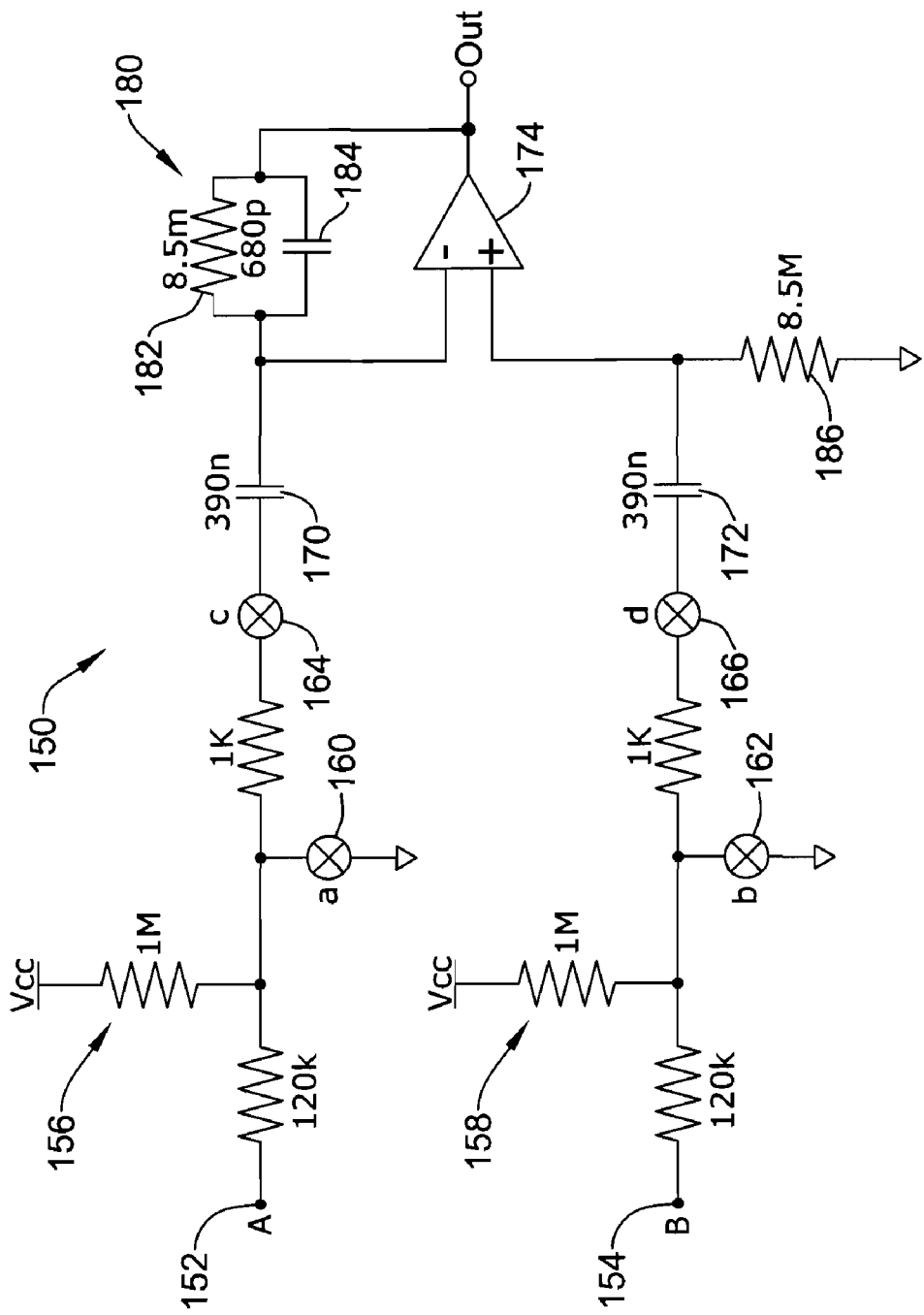
FIG. 3 is a circuit schematic illustrating input circuitry for an illustrative device.

FIG. 3 is a circuit schematic having input circuitry for an illustrative device. It should be understood that a switching array 102 as shown in FIG. 2 may be included, but is omitted to allow greater detail to be shown in the rest of the input circuitry. The input circuitry 150 is shown as including inputs A 152 and B 154, each defining a leg of the input circuitry 150. Shown as 156, 158, pull-up circuitry is used in each leg, and various coupling impedances are included. These parameters may be changed as suits an individual system and application.

Ground switches a, b are shown at 160, 162, and isolation switches c, d are shown at 164, 166. The use of switches 160, 162, 164, 166 is further explained relative to FIG. 4. Any suitable switching devices may be used. Relatively large capacitors 170, 172 are used as DC-blocking coupling capacitors. The illustrative ECG Amplifier 174 receives signal as a differential input. A low pass feedback filter 180 is shown including a resistor 182 and capacitor 184. Again, a resistor 186, shown as an 8.5 megohm resistor, couples the noninverting input to ground.

In an illustrative example, the circuit provides a cutoff frequency in the range of about 40 Hertz. The illustrative values shown and the cutoff frequency may vary. At a low frequency the effective impedance of the filter is dominated by the resistor 182, but remains at least in the range of several megaohms. Due to this high effective impedance, following delivery of a stimulus or a change in sensing vector any change that is brought across the coupling capacitors 170, 172 to the inputs of the ECG Amplifier 174 is slowly dissipated. In an illustrative embodiment using the above filter, if the coupling capacitor 170 has an impedance of 390 nanofarads, the RC time constant for purposes of large signal charging/discharging of coupling capacitor 170 is in the range of 3.3 seconds at DC (giving a cutoff frequency for the DC blocking circuitry of about 0.3 Hertz). The noninverting input has a similarly slow large signal response as it returns to ground when current flows through resistor 186. Therefore, any large disturbance in the DC state of the electrodes coupled to inputs A 152 and B 154 may take a significant amount of time to dissipate.

One approach to reducing the feedback loop time constant would be to use smaller resistors 182, 186. However, to achieve the same cutoff frequencies in the circuit, larger capacitors would be needed, taking up valuable space in the implanted medical device. Furthermore, smaller resistive values would increase current flow, thereby increasing power consumption. Therefore, a solution that does not limit the selection of passive circuit elements (resistors and capacitors) is desirable.

Figure 4:
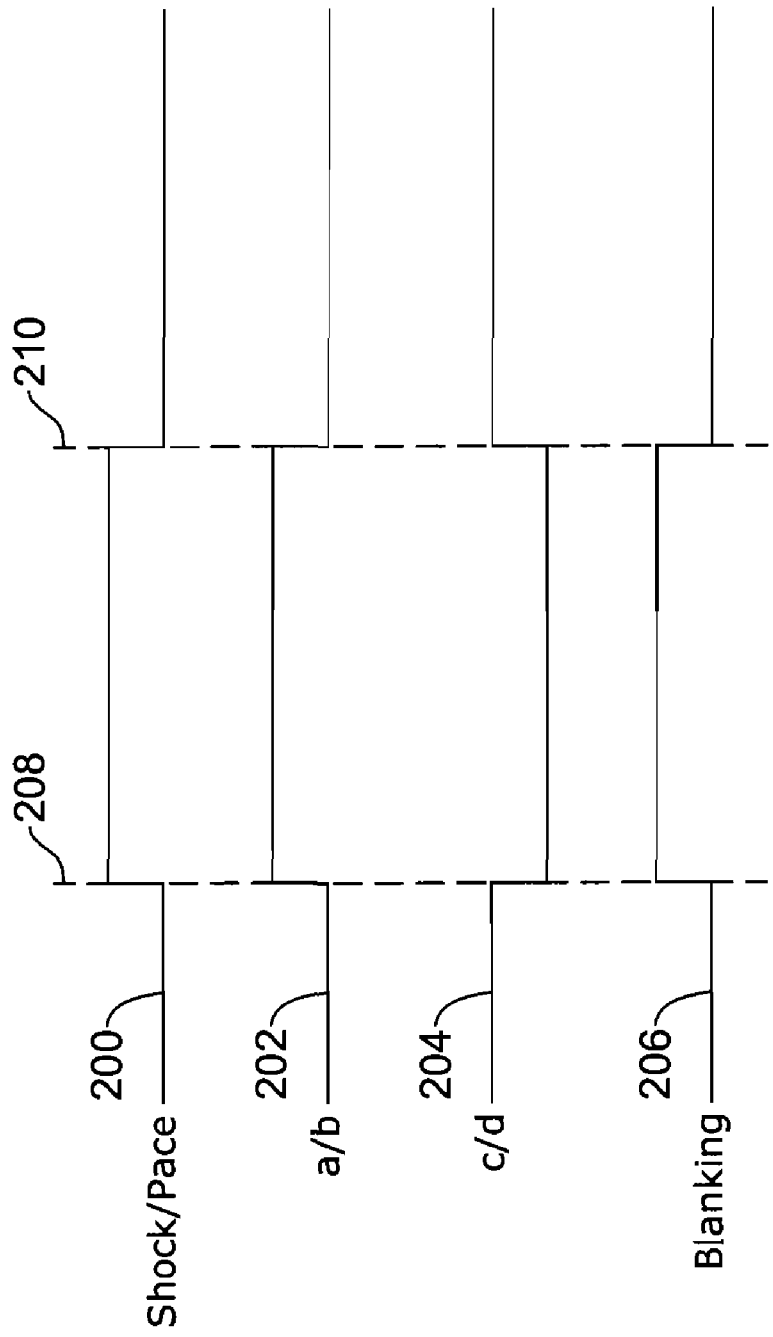
FIG. 4 is a timing diagram illustrating operation of the circuit of FIG. 3.

FIG. 4 is a timing diagram illustrating operation of the circuit of FIG. 3. Four variables are shown as having either a low or high value. Line 200 indicates whether a stimulus is being delivered when the line is high. Line 202 indicates that ground switches a, b 160, 162 (FIG. 3) are closed when the line 202 is high. Line 204 indicates that coupling switches c, d 164, 166 (FIG. 3) are closed when the line 204 is high. Line 206 indicates whether blanking is occurring when the line is high.

At time 208, a stimulus is delivered, as indicated by line 200 going high. Simultaneously, ground switches a, b 160, 162 (FIG. 3) are closed, coupling switches c, d 164, 166 (FIG. 3) are opened, and blanking begins, as indicated by lines 202, 204, 206, respectively. During shock delivery, incoming signal is ignored as indicated by the blanking period. Also during shock delivery, the inputs to the ECG Amplifier are isolated from the high voltage caused by stimulus delivery by opening the coupling switches c, d, 164, 166 (FIG. 3) and closing the ground switches a, b, 160, 162 (FIG. 3).

After the stimulus is delivered, as shown at time 210, the stimulus line 200 returns to a low position, ground switches a, b 160, 162 (FIG. 3) open, coupling switches 164, 166 (FIG. 3) close, and the blanking period ends. It should be noted that actual stimulus delivery may end prior to time 210. In some embodiments, the period between time 208 and 210 may be in the range of 50 milliseconds, although shorter and longer time periods may be used as well.

Figure 5A:
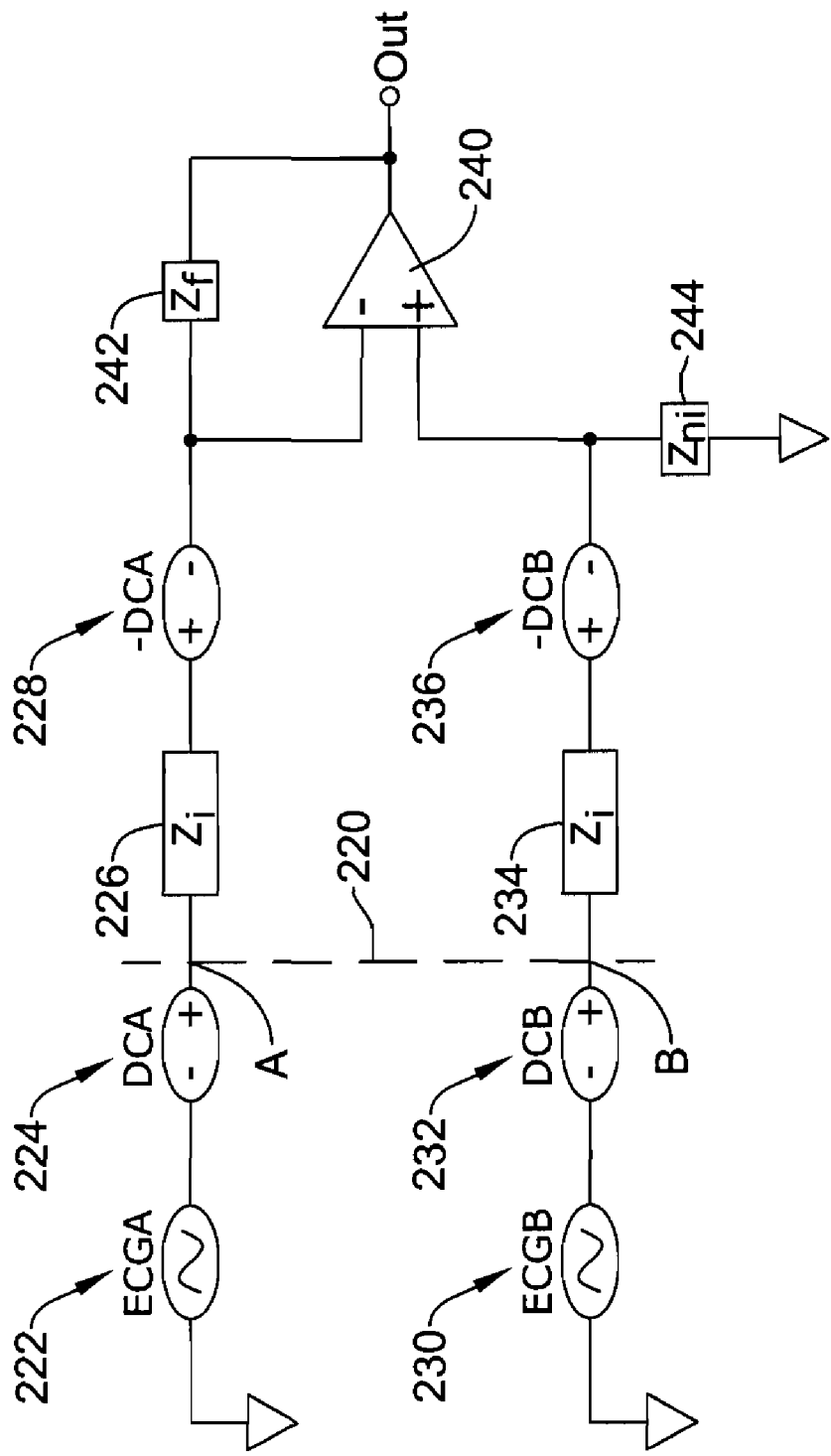
FIGS. 5A-5B model pre-shock and post-shock states of the input circuitry of FIG. 3.
Figure 5B:
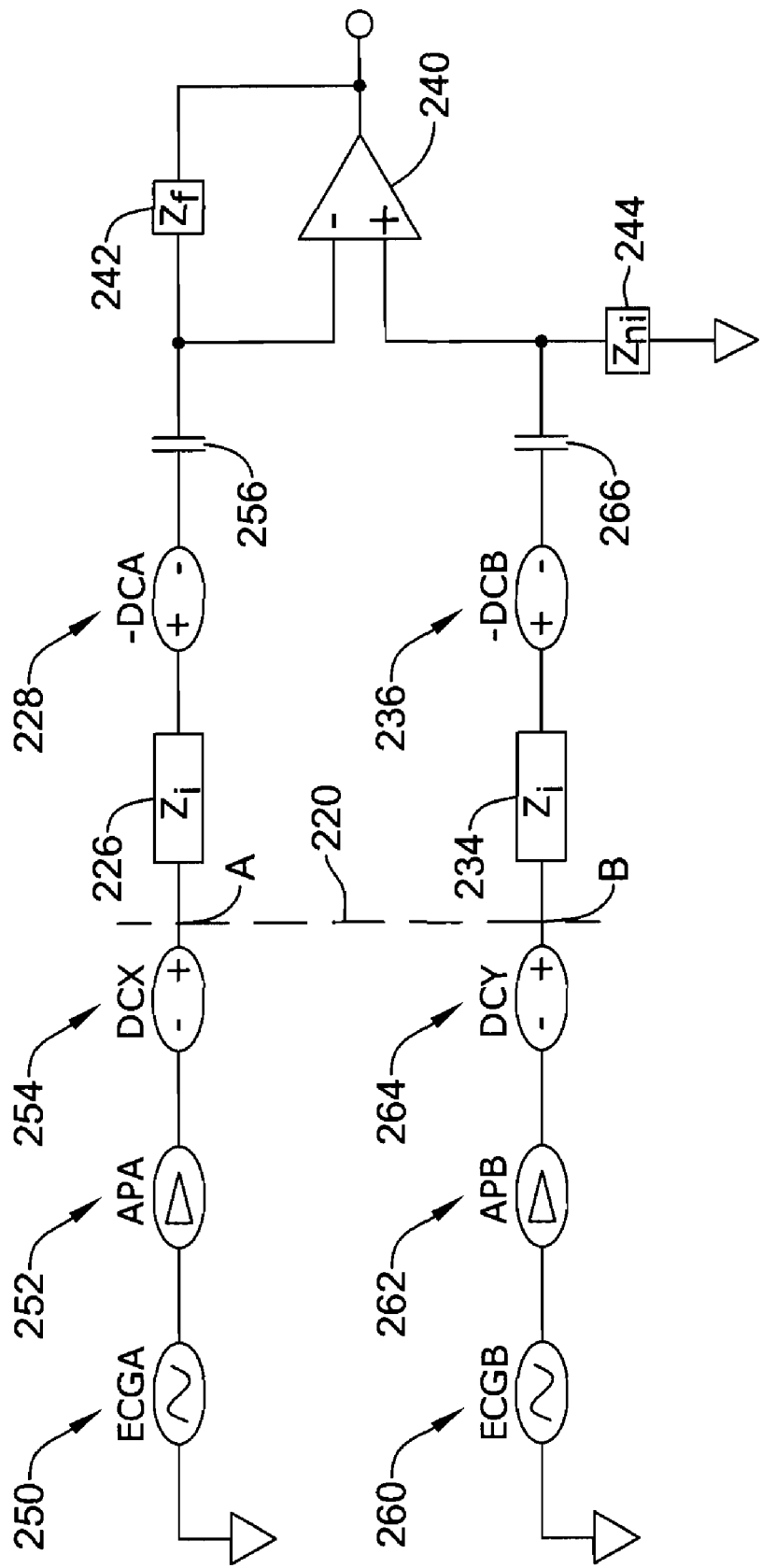

FIGS. 5A-5B model pre-shock and post-shock states of the input circuitry of FIG. 3. The switches are omitted from FIG. 5A, when compared to FIG. 3. Line 220 separates that which occurs outside of the input circuitry of FIG. 3 from the input circuitry, and nodes A and B correspond to A and B 152, 154 of FIG. 3.

The signal that is received by the input circuitry at A is shown as including a small signal component ECGA 222 and a DC component DCA 224 related to patient physiology and the interface between the electrode and its surroundings. This signal is received by the input circuitry, passing through an input impedance $Z_i$ 226. The coupling capacitor 170 (FIG. 3) is shown illustratively as −DCA 228, a voltage that is equal to and opposite of DCA 224. Thus the small signal ECGA 222 reaches the inverting input of the ECG Amplifier 240, which is shown illustratively in association with feedback filter $Z_f$ 242. In like fashion, node B receives a small signal component ECG B 230, and a DC component DCB 232. This signal passes an input impedance $Z_i$ 234. Again the coupling capacitor 172 (FIG. 3) is shown illustratively as −DCB 236, which removes the signal DCB 232, leaving small signal 230 to reach the noninverting input 240 of the ECG Amplifier 240. Again, an impedance 244 couples the noninverting input of the ECG Amplifier 240 to ground.

Because the electrodes may be positioned apart from one another in the patient, it is likely that DCA 224 and DCB 232 will not be equal. The difference between voltages DCA 224 and DCB 232 represent the input offset voltage of the steady state system. While modeled as DC values, it should be understood that any potential within the patient's body at either electrode that moves slowly enough to be filtered by the coupling capacitors will be encompassed by DCA 224 and/or DCB.

As can be seen from FIG. 5A, the steady state accounts for DC characteristics at the electrodes using DC values stored on the coupling capacitors, and allows small signal operation. However, after a shock is applied, or after some other change such as a change of sensing vector, the state shown in FIG. 5B arises. The drawing is somewhat similar to that of FIG. 5A, including nodes A and B. However, detailed review illustrates that this configuration may have difficulty quickly achieving small signal operation.

Looking to the signal arriving at node A, the signal now includes ECGA 250, an After potential A (APA) 252, and DCX 254. Stimulus delivery tends to cause an afterpotential that may slowly decay and which is modeled as APA 252. Also, for various reasons, the DC state of the system may change, leading to the substitution of DCX 254 for DCA shown in FIG. 5A. For example, delivery of a charge may affect the tissue itself, or may cause the formation of charge traps at the tissue/electrode interface, either of which can create a lasting change in the DC state of the system.

The signal received at A goes through the input impedance $Z_i$ 226 and is offset against −DCA 228, which represents the voltage previously stored on the capacitor 256 before application of the stimulus. The capacitor 256 does not instantaneously provide a change in the voltage it stores. Instead, current must be received or discharged to change the voltage on the capacitor 256.

In similar fashion, the signal arriving at node B includes ECG B 260, APB 262, and DCY 264. This signal passes through the input impedance $Z_i$ 234 and is offset by the previously stored voltage, −DCB 236 that had been stored on the capacitor 266. This side of the input circuitry is not attached to the feedback loop 242 for the amplifier 240, and so changes occurring due to APB 262 and DCY 264 are accounted for by changing the voltage on capacitor 266 via the resistor 244.

Not only are several voltages not known at this point in time, but some of the voltages are changing. In particular, afterpotentials APA and APB 252, 262 are likely to be decaying voltages, while the inclusion of the input impedances $Z_i$ 226, 234, taken in combination with the coupling capacitances, creates yet another time constant, this time relating to the period of time it would take, if the voltages outside of the input circuitry were not changing, for the coupling capacitors to offset voltages APA, APB 252, 262 and DCX 254 and DCY 264. At this point, the input offset voltage has changed to the difference between APA 252 plus DCX 254, and APB 262 plus DCY 264. The change in the input offset voltage is thus:

Change=(DCA−DCB)−((APA+DCX)−(APB+DCY))

Actual calculation of the change is not necessary for the purposes herein, but it can be seen that the resultant change includes several variables. If, instead of a shock delivery, a sensing vector change occurs, the above modeling remains the same except that APA 252 and APB 254 may be omitted.

The output of the ECG Amplifier 240 will reach saturation if Change multiplied by the gain of the ECG Amplifier 240 is greater than the dynamic output range of the ECG Amplifier 240. In an illustrative system operating between 0 and 3 volts, the output of the ECG Amplifier 240 will be either 0 volts or 3 volts when it is saturated. With the output saturated, coupling capacitor 256 will be either charged or discharged until a steady state can be reached and small signal operation resumes. Meanwhile, the voltage at the noninverting input slowly returns to ground as current flows through resistor 244. However, as discussed with reference to FIG. 3, the time constant of $Z_f$ 242 in combination with coupling capacitor 256 may be quite large, preventing a quick return to the small signal operation. An improved manner of reaching small signal operation would be useful.

Figure 6:
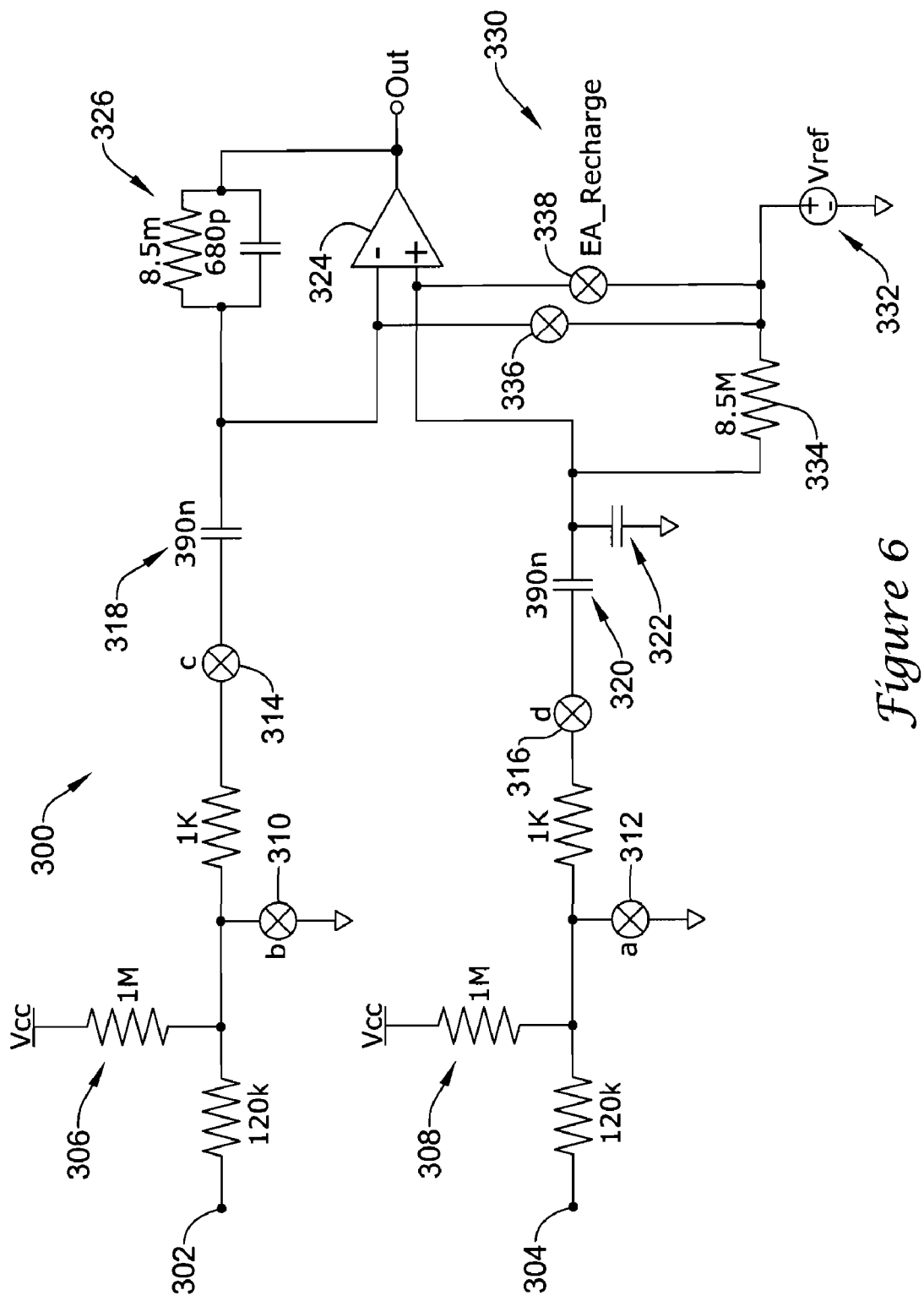
FIG. 6 is a circuit schematic illustrating input circuitry including a recharge circuit.

FIG. 6 is a circuit schematic illustrating input circuitry including a recharge circuit. The input circuitry 300 again is shown with nodes A 302 and B 304. Pull-up circuitry 306, 308 is provided to each input. Ground switches a 312 and b 314, as well as isolation switches c 314 and d 316 are included again. Coupling capacitors 318, 320 are shown as before as well, with these coupling to the inputs of the ECG Amplifier 324. Again a feedback loop includes a low pass RC filter 326. In addition, the circuit of FIG. 6 also illustrates a capacitor 322 coupling the noninverting input of the ECG Amplifier 324 to ground.

The circuit of FIG. 6 also includes a recharge circuit 330 including a reference voltage source 332 that may be a buffered voltage output, such as a buffered voltage regulator output, a digital-to-analog conversion output, or some other reference voltage source having relatively low output impedance. In place of a resistor to ground, as shown in FIGS. 2-3 and 5A-5B, an impedance 334 couples the noninverting input of the ECG Amplifier 324 to the reference voltage source 332. The inclusion of the impedance 334 allows the voltage at the noninverting output to vary over time, but, given steady state operation, eventually the voltage at the noninverting output will return to that of the reference voltage source 332.

Also illustrated are ECG Amplifier recharge switches 336, 338 that couple the buffer 332 to each of the inverting and noninverting inputs of the ECG Amplifier 324. One ECG Amplifier recharge switch 338 bypasses the coupling resistor 334 with respect to the noninverting input. By closing switches 336, 338 during a selected time period following stimulus delivery, the voltages stored on the coupling capacitors 318, 320 are quickly reset or recharged to render the inputs to the ECG Amplifier 324 within a range for small signal operation. The recharge circuit can thus accommodate or compensate for afterpotential resulting from stimulus delivery and/or any other change in the input offset voltage. The effective impedance for the recharge circuit can be approximated as the sum of the 120 k and 1 k resistors shown, along with the output impedance of the buffer, and the lead and tissue impedance between nodes 302 and 304. Barring lead failure, this impedance will be much less than the 8.5 megohm resistances that are otherwise encountered with the feedback circuit 326 and/or resistor 334.

During operation of the recharge circuit, the switches 336, 338 can be closed, coupling the reference voltage source 332 directly to a first node defined between the first coupling capacitor 318 and the inverting input to the ECG Amplifier 324, as well as to a second node defined between the second coupling capacitor 320 and the noninverting input to the ECG Amplifier 324. In the embodiment shown, there will be virtually no impedance in either circuit path (except for any impedance of the line itself and the switches 336, 338). In an alternative embodiment, a relatively small impedance may be included in one or both paths from the reference voltage source 332 to either input to the ECG Amplifier 324, if desired.

Figure 7:
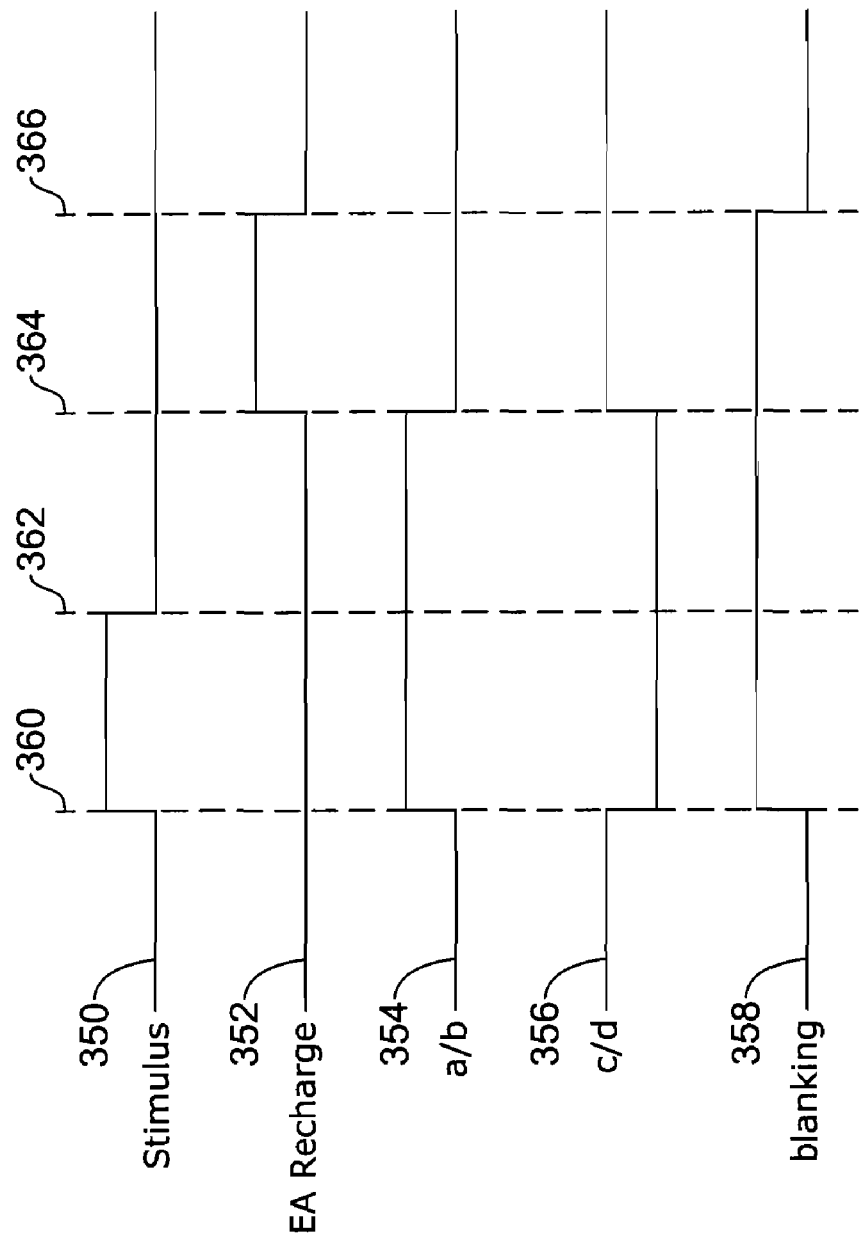
FIG. 7 is a timing diagram illustrating operation of the circuit of FIG. 6.

FIG. 7 is a timing diagram illustrating operation of the circuit of FIG. 6. Lines are shown as follows: stimulus 350, EA recharge switches 352, ground switches a/b 354, coupling switches c/d 356, and blanking indicator 358. At time 360, stimulus delivery starts as indicated on stimulus line 350. In association with the stimulus delivery, the ground switches a/b close, as indicated on line 354, and coupling switches c/d open as indicated on line 356. Stimulus delivery is completed at 362, as indicated on line 350. In an illustrative example, the period between lines 360, 362 lasts about 50 milliseconds.

The ground switches remain closed and the coupling switches remain open until time 364, as indicated at lines 354, 356. In an illustrative example, the period between lines 362, 364 may be in the range of 50 milliseconds. This allows for some settling of afterpotential following stimulus delivery, although it is likely that an afterpotential will remain. At time 364, the ECG Amplifier is reconnected to the rest of the input circuitry by opening the ground switches and closing the coupling switches, as indicated at lines 354, 356. The EA recharge switches are closed at time 364, as indicated on line 352, and remain closed until time 366. At time 366, the EA recharge switches open, and the blanking period ends, as shown at lines 352, 358. In an illustrative example, the period between times 364, 366 is about 200 milliseconds.

Each of the time periods between times 360, 362, 364 and 366 may vary in other embodiments. For example, the blanking period may extend beyond time 366, after the EA recharge switches have opened, allowing for more settling of the sensing input circuitry. The effect of the EA Recharge circuit is further illustrated in FIG. 8.

Figure 8:
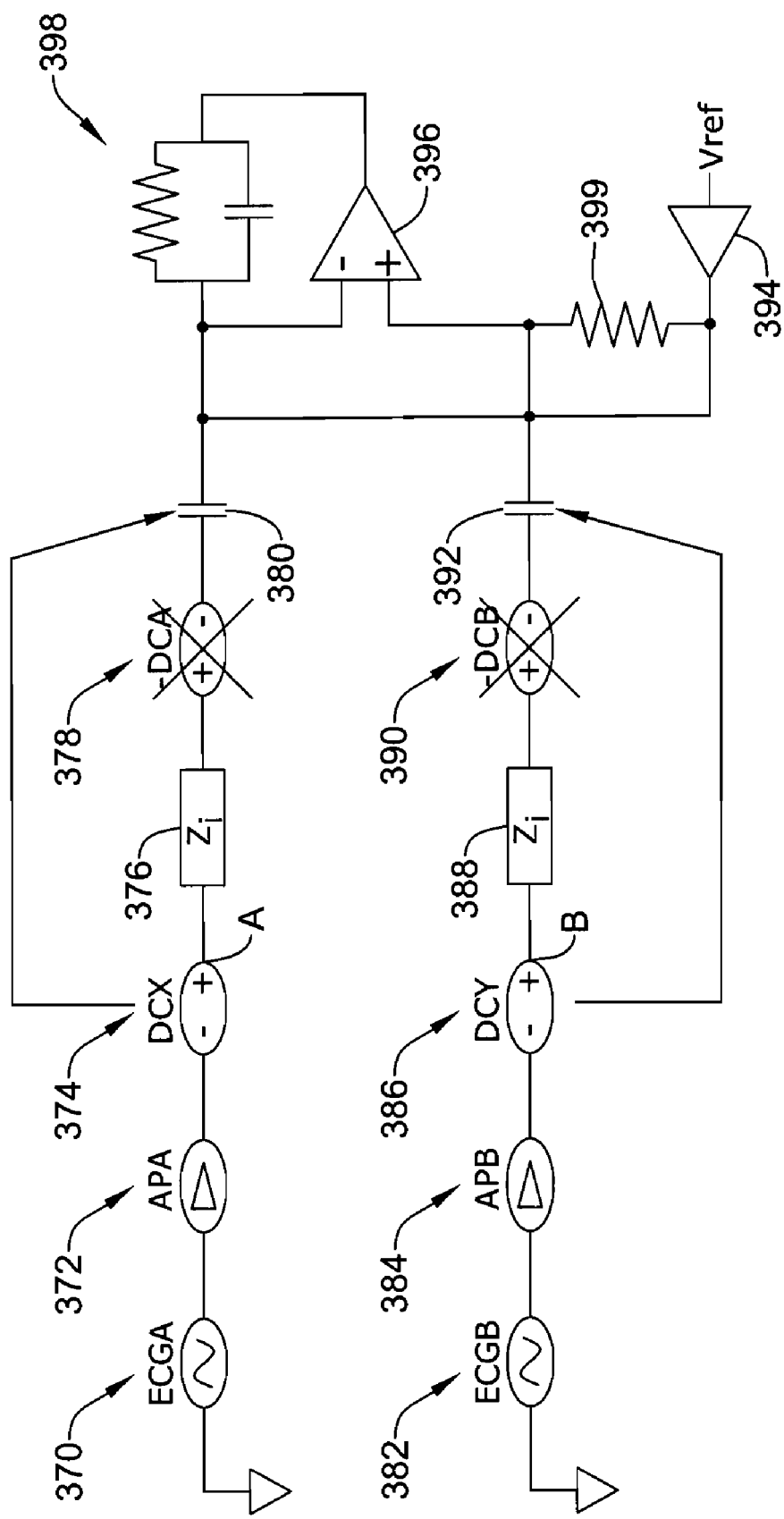
FIG. 8 illustrates a post-shock state of the input circuitry of FIG. 6.

FIG. 8 illustrates a post-shock state of the input circuitry of FIG. 6. The reference voltage source is shown as a buffered reference voltage 394, which is one manner of providing a reference voltage source. The model shown corresponds to the period between times 364, 366 (FIG. 7) when the ECG Amplifier recharge switches 336, 338 (FIG. 6) are closed, applying the recharge circuit 330 (FIG. 6). The input circuitry receives a similar voltage as before, including components ECGA 370, APA 372, and DCX 374 at node A, and components ECGB 382, APB 384 and DCY 386 at node B. Each passes through respective input impedances $Z_i$ 376, 388.

The inclusion of the low output impedance reference voltage via buffered reference voltage source 394 means that the previously stored DC voltages, −DCA 378 and −DCB 390, are removed from the coupling capacitors 380, 392. Instead, the coupling capacitors 380, 392 are charged by the buffered reference source 394 to provide a voltage difference across each that accounts for the difference between the reference voltage and DCX 374 on capacitor 380, and the difference between the reference voltage and DCY 386 on capacitor 392. The circuit does not rely on a current passing through the relatively larger impedances of the circuit to account for DCX 374, −DCA 378, DCY 386, and −DCB 390, and so the recovery to small signal operation is much quicker.

The timing is set up so that the buffered reference voltage source 394 has adequate time to charge the capacitors 380, 392 to reach a relatively steady state condition. While the buffered reference voltage source 394 is coupled to the capacitors 380, 392, the amplifier 396 would have a null input, as the inverting input is shorted to the noninverting input. The output of the amplifier 396 may be either high or low, but will not affect the buffer 394 operation due to the large resistance in the filter 398. In an illustrative example, the reference voltage is selected to be between the range of potentials used to power the ECG Amplifier. For example, in a system having a power supply defined from ground to +3 volts, the reference voltage may be about 1.5 volts, or any other suitable voltage within the range defined by the power supply.

To the extent that the afterpotentials APA 372 and APR 384 may continue to move/dissipate after termination of EA recharge, the feedback filter 398 and resistor 399 may address this slowly changing voltage. In some embodiments, additional methods, particularly in the programming and/or addition of extra filters may be used to address the afterpotentials.

Some illustrative examples of methods and devices adapted to address afterpotentials and reduce effects on event detection are shown in U.S. patent application Ser. No. 11/497,204, filed Aug. 1, 2006, published as US 2008-0045850 A1, and titled IMPLANTABLE MEDICAL DEVICES USING HEURISTIC FILTERING IN CARDIAC EVENT DETECTION, the disclosure of which is incorporated herein by reference.

Figure 9:
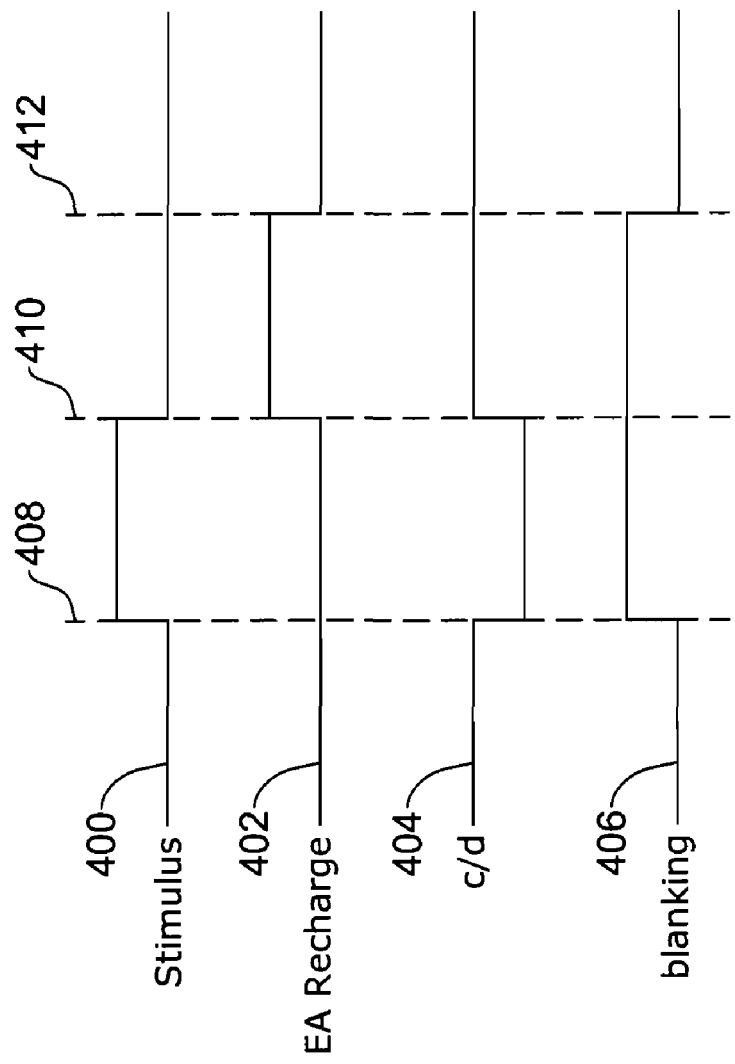
FIG. 9 is a timing diagram illustrating another method of operating the circuit of FIG. 6.

FIG. 9 is a timing diagram illustrating another method of operating the circuit of FIG. 6. Lines are shown as follows: stimulus 400, EA recharge 402, coupling switches c and d 404, and blanking indicator 406. At time 408, stimulus is initiated as indicated by stimulus line 400. At this time, the coupling switches open, as indicated by line 404, and the blanking period begins as indicated by line 406. At time 410, the stimulus is over as indicated by line 400. The coupling switches close again, as indicated by line 404, and the EA recharge circuit is applied, as indicated by line 402. Later, at time 412, the EA recharge circuit is decoupled as indicated by line 402, and the blanking period ends as shown by line 406. In the illustrative embodiment of FIG. 9, there is no need for the ground switches, although these may be included if desired. Further, an initial period of delay before application of EA recharge is omitted.

The embodiment shown in FIG. 9 may be useful when a lower amplitude stimulus is applied as, for example, occurs when a pacing stimulus is delivered. Comparing the method of FIG. 9 to that of FIG. 7, the delay between time 362 and time 364 in FIG. 7 may be treated as an allowance for physiological relaxation of afterpotential after a high amplitude stimulus. For example, immediate application of the recharge circuit after a large stimulus may lead to a circumstance where the external relaxation of the afterpotential occurs faster than the feedback loop can accommodate, which would be an over-reaction to the afterpotential. With a lower amplitude stimulus, such as a pacing stimulus, this becomes less likely and the delay before application of the recharge circuit may be omitted. As before, other variations may occur in additional embodiments. For example, the blanking period may extend beyond the EA recharge period. Also, for example, the duration of the blanking period and/or the EA recharge period may vary depending upon the type of stimulus provided. For example, a longer EA recharge period and/or longer blanking period may be provided after a higher amplitude stimulus is delivered, and a shorter EA recharge period and/or a shorter blanking period may follow delivery of a pacing stimulus.

Figure 10:
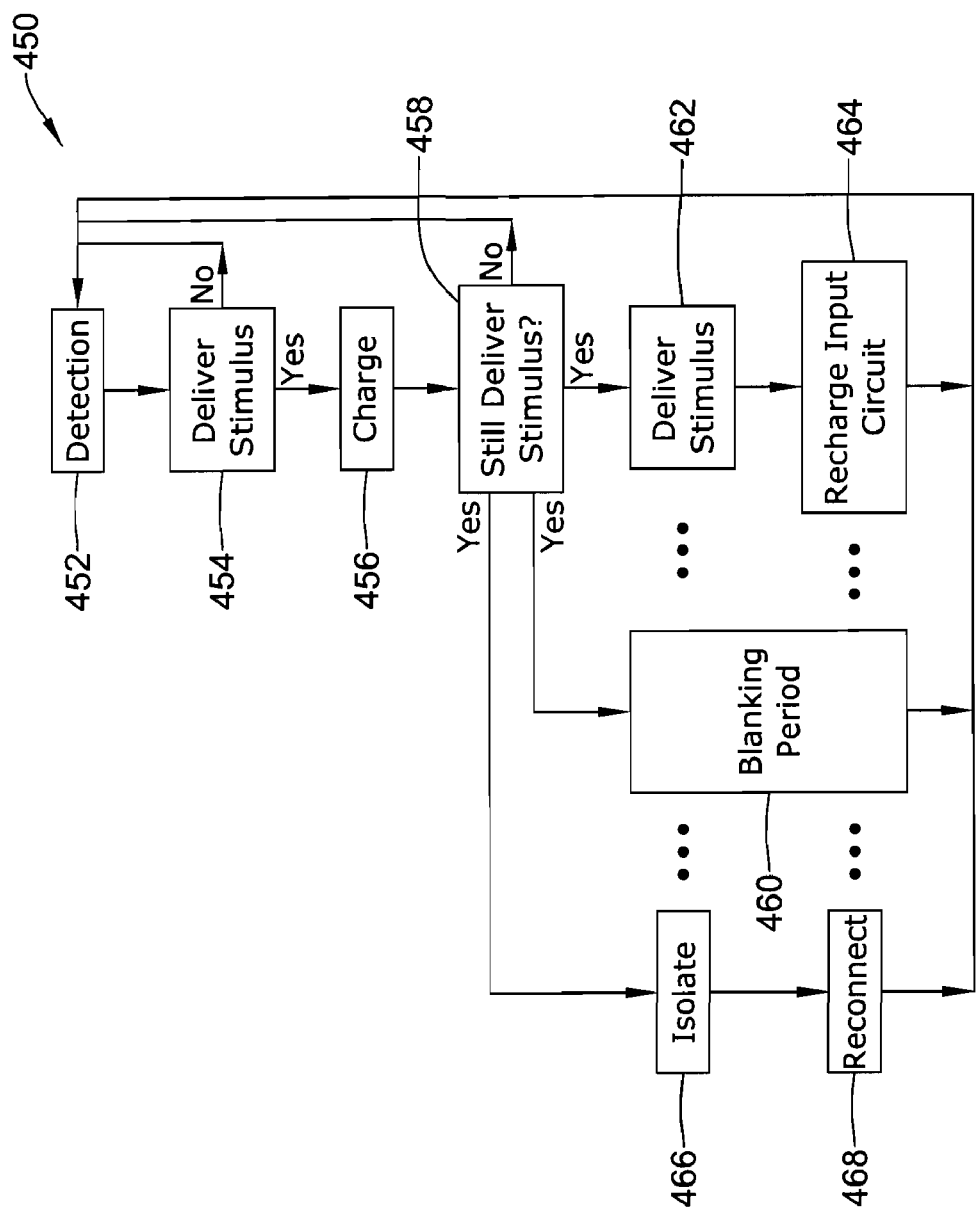
FIG. 10 is a block diagram showing an illustrative method.

FIG. 10 is a block diagram showing an illustrative example method of delivering defibrillation or cardioversion energy to a patient from an implanted system. The method 450 illustrates an overall approach. A detection of a cardiac event occurs as shown at 452. Based on characteristics of the detection 452, a determination is made of whether or not to deliver stimulus to the patient, as shown at 454. If it is determined that no stimulus is needed at 454, the method returns to 452 and waits for a next detection. There are various methods for making such a determination. Some illustrative embodiments are disclosed in U.S. patent application Ser. No. 10/856,084, titled METHOD FOR DISCRIMINATING BETWEEN VENTRICULAR AND SUPRAVENTRICULAR ARRHYTHMIAS, published on Dec. 16, 2004 as US-2004-0254613-A1 and now U.S. Pat. No. 7,330,757, the disclosure of which is incorporated herein by reference.

If a decision is made to deliver stimulus at 454, the method continues by charging the power capacitors in the system to a defibrillation or cardioversion voltage, as shown at 456. Various methods and circuits for charging the power capacitors for delivering a defibrillation or cardioversion stimulus are known and need not be explained here. Optionally, an additional check on whether stimulus should still be delivered may be performed at 458 and, if not, the method returns to 452 and awaits a next detection.

If stimulus is still to be delivered at 458, several steps occur in parallel. As shown at 460, a blanking period is initiated, during which analysis of incoming signal may not occur. At the same time, the stimulus is delivered, as shown at 462. After stimulus delivery, the illustrative method recharges the input circuit, as shown at 464. Step 464 also occurs during the blanking period. During the delivery of the stimulus in step 462, another step occurs as shown at 466, which indicates that at least some of the input circuit is isolated from the sensing electrodes during stimulus delivery. After stimulus delivery, the input circuit is reconnected, as indicated at 468. The step of recharging the input circuit 464 may occur while the input circuit is reconnected.

In another illustrative embodiment, a pacing stimulus may be delivered. If a pacing stimulus is delivered, the method 450 may be simplified, excluding steps 452, 456 and 458, with decision block 454 simply being a determination that a pacing stimulus is to be applied. The blanking period 460 and the steps of delivering stimulus 462 and recharging the input circuit 464 may be performed as above. If a pacing stimulus is applied, the steps of isolating 466 and reconnecting 468 may also be included, although these may also be omitted, if desired.

Figure 11:
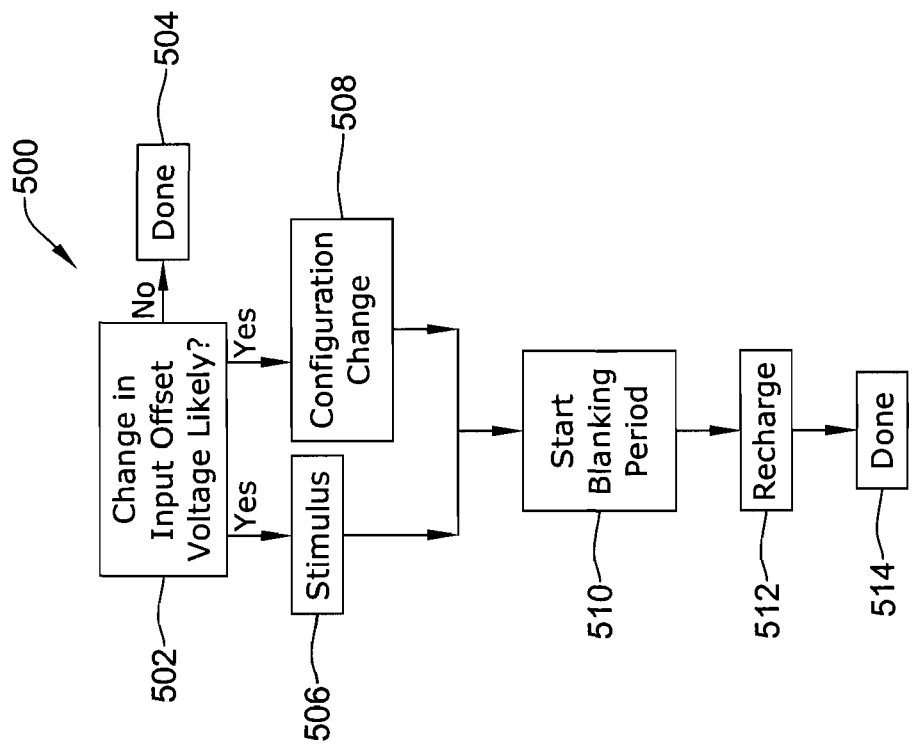
FIG. 11 is a block diagram showing another illustrative method.

FIG. 11 is a block diagram for another illustrative method. The method 500 begins with a determination of whether a change in the input offset voltage is likely, as shown at 502. The input offset voltage is the potential difference, at or near DC, between the electrodes used to perform sensing in the patient. If no such change is likely, the method ends as indicated at 504.

The illustrative method identifies at least two circumstances that can render a change in the input offset voltage likely. First, if a stimulus (defibrillation, cardioversion, or pacing) is delivered to the patient, a change in the input offset voltage is likely, as indicated at 506. Second, if there is a change in the sensing configuration, a change in the input offset voltage is likely, as indicated at 508.

In either event 506, 508, the method continues at 510 where a blanking period is started. Next, and during the blanking period, the recharge circuit is operated as indicated at 512. The method then ends, as indicated at 514.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An implantable cardiac stimulus device comprising:
input circuitry for receiving a signal;
electrodes coupled to the input circuitry to provide a cardiac signal for analysis; and
a recharge circuit coupled to the input circuitry;
wherein an input offset voltage occurs at the input circuitry; and
wherein the implantable cardiac stimulus device is configured to:
identify whether a change in the input offset voltage is likely; and
if so, operate the recharge circuit to accommodate changes to the input offset voltage;

wherein the input circuitry comprises coupling capacitors, wherein the recharge circuit is coupled to the coupling capacitors;
the input circuitry further comprises an ECG Amplifier for amplifying signal from the electrodes;
a first of the coupling capacitors is disposed in series with a first input of the ECG Amplifier and a second of the coupling capacitors is disposed in series with a second input of the ECG Amplifier, both relative to inputs from the electrodes;
the recharge circuit is selectively coupled to a first node defined between the first coupling capacitor and the first ECG Amplifier input;
the recharge circuit is selectively coupled to a second node defined between the second coupling capacitor and the second ECG Amplifier input; and
when the recharge circuit is operated, the recharge circuit is coupled to the first and second nodes via a relatively low impedance or no impedance.

2. The implantable cardiac stimulus device of claim 1, wherein the implantable cardiac stimulus device is configured to identify whether a change in the input offset voltage is likely by determining whether a stimulus has been provided to a patient.

3. The implantable cardiac stimulus device of claim 1, wherein:
the electrodes define multiple sensing vectors for sensing cardiac activity of a patient;
the input circuitry is configured with one or more switches for selecting a sensing vector; and
the implantable cardiac stimulus device is configured to identify whether a change in the input offset voltage is likely by determining whether a change in the selected sensing vector has occurred.

4. The implantable cardiac stimulus device of claim 1, wherein the input circuitry comprises a frequency selective filter having an impedance and the recharge circuit comprises a reference voltage source output having relatively low impedance when compared to the impedance of the frequency selective filter.

5. The implantable cardiac stimulus device of claim 1 wherein, when the recharge circuit is selectively coupled to the first node and the second node, the inputs to the ECG Amplifier are shorted together via the recharge circuit.

6. An implantable cardiac stimulus device comprising:
input circuitry for receiving a signal;
electrodes coupled to the input circuitry to provide a cardiac signal for analysis; and
a recharge circuit coupled to the input circuitry for accommodating post-shock after potential;
wherein the implantable cardiac stimulus device is configured to:
observe cardiac function of a patient,
determine whether stimulus is appropriate,
deliver stimulus when appropriate, and
after delivering stimulus, operate the recharge circuit;
the input circuitry comprises coupling capacitors and the recharge circuit is coupled to the coupling capacitors;
the input circuitry further comprises an ECG Amplifier for amplifying signal from the electrodes;
a first of the coupling capacitors is disposed in series with a first input of the ECG Amplifier and a second of the coupling capacitors is disposed in series with a second input of the ECG Amplifier;
the recharge circuit is selectively coupled to a first node defined between the first coupling capacitor and the first ECG Amplifier input;
the recharge circuit is selectively coupled to a second node defined between the second coupling capacitor and the second ECG Amplifier input; and
the implantable cardiac stimulus device is further configured such that, when the recharge circuit is operated, the recharge circuit is coupled to the first and second nodes via a relatively low impedance or no impedance.

7. The implantable cardiac stimulus device of claim 6, wherein the input circuitry comprises a frequency selective filter having an impedance and the recharge circuit comprises a reference voltage source having relatively low impedance when compared to the impedance of the frequency selective filter.

8. The implantable cardiac stimulus device of claim 6 wherein, when the recharge circuit is selectively coupled to the first node and the second node, the inputs to the ECG Amplifier are shorted together via the recharge circuit.

9. A method of operating a cardiac stimulus device implanted in a patient:
the device comprising at least first and second electrodes configured to electrically sense cardiac activity by the patient, the first and second electrodes being selectively coupled to an ECG Amplifier for amplifying signal from the first and second electrodes via input circuitry including coupling capacitors;
the method comprising:
providing a recharge circuit coupled to the coupling capacitors;
delivering a stimulus to the patient;
during the stimulus delivery, isolating the ECG Amplifier from the first and second electrodes; and
following stimulus delivery, operating the recharge circuit to accommodate changes in DC status of the system following stimulus delivery,
wherein:
the ECG Amplifier includes first and second inputs and the coupling capacitors include a first coupling capacitor coupled to the first ECG Amplifier input and a second capacitor coupled to the second ECG Amplifier input;
the first and second coupling capacitors have an electrode side and an ECG Amplifier side, the ECG Amplifier side of each of the coupling capacitors being coupled to the ECG Amplifier, and
the recharge circuit comprises a voltage source selectively coupled to the ECG Amplifier sides of the first and second coupling capacitors such that, when the recharge circuit is operated to accommodate changes in DC status of the system, the first and second inputs to the ECG Amplifier are shorted together.

10. The method of claim 9, further comprising analyzing cardiac signals and providing a blanking period comprising:
a first time period corresponding to the stimulus delivery;
a second time period immediately after stimulus delivery; and
a third time period following the second time period, the third time period corresponding to operation of the recharge circuit.

11. A method of operating an implanted cardiac stimulus device, the implanted cardiac stimulus device including input circuitry for receiving a signal and electrodes coupled to the input circuitry to provide a cardiac signal for analysis wherein an input offset voltage occurs at the input circuitry, the method comprising:
identifying whether a change in the input offset voltage is likely, and if so,
operating a recharge circuit to accommodate a change in the input offset voltage;

wherein the input circuitry includes an ECG Amplifier having first and second inputs and first and second coupling capacitors coupled to the first and second inputs, Respectively, of the ECG amplifier; and wherein the step of the operating the recharge circuit includes selectively coupling the recharge circuit to the first and second inputs of the ECG Amplifier, shorting the first and second inputs together and charging/discharging the first and second coupling capacitors.

12. The method of claim 11, wherein the step of identifying whether a change in the input offset voltage is likely includes determining whether a stimulus has been provided to a patient.

13. The method of claim 11, wherein:
the electrodes define multiple sensing vectors for sensing cardiac activity of a patient;
the input circuitry is configured with one or more switches for selecting a sensing vector; and
the step of identifying whether a change in the input offset voltage is likely includes determining whether a change in the selected sensing vector has occurred.

* * * * *